United States Patent [19]
Wong et al.

[11] Patent Number: 5,281,622
[45] Date of Patent: Jan. 25, 1994

[54] METHOD OF TREATING INFLAMMATION AND PAIN WITH 2-(N-SUBSTITUTED-AMINOALKYL)-5-(E)-ALKYLIDENE CYCLOPENTANONES, 2-(N-SUBSTITUTED-AMINOALKYL)-5-(E)-ARYLALKYLIDENE CYCLOPENTANONES, AND DERIVATIVES THEREOF

[75] Inventors: Lan K. Wong, Pittsburgh, Pa.; Hai-Tao Chen; Zhi-Zhong Ji, both of Shenyang, China

[73] Assignee: University of Pittsburgh of the Commonwealth System of Higher Education, Pittsburgh, Pa.

[21] Appl. No.: 44,983

[22] Filed: Apr. 8, 1993

Related U.S. Application Data

[62] Division of Ser. No. 847,910, Apr. 3, 1992, Pat. No. 5,250,735.

[51] Int. Cl.$^5$ .................. A61K 31/12; A61K 31/36; A61K 31/265
[52] U.S. Cl. .................. 514/464; 514/512; 514/659; 514/666; 514/690
[58] Field of Search .............. 514/690, 659, 665, 464, 514/512

[56] References Cited

U.S. PATENT DOCUMENTS

| | | | |
|---|---|---|---|
| 3,269,942 | 8/1966 | Wilks | 210/64 |
| 3,852,296 | 12/1974 | Viterbo et al. | 514/530 |
| 4,766,147 | 8/1988 | Noyori et al. | 514/530 |
| 4,904,640 | 2/1990 | Markert et al. | 568/379 |

OTHER PUBLICATIONS

K. H. Lee et al., "Cytotoxicity of Sesquiterpene Lactones", Cancer Research, vol. 31, 1649-1654, Nov. 1971.
S. M. Kupchan et al., "Tumor Inhibitors. 69. Structure–Cytotoxicity Relationships among the Sesquiterpene Lactones", Journal of Medicinal Chemistry, vol. 14, No. 12, 1147-1152, Dec. 1971.
G. A. Howie et al., "Potential Antitumor Agents. Synthesis of Bifunctional α-Methylene-γ-butyrolactones", Journ. of Med. Chem., vol. 19, No. 2, 309-313, 1976.
J. M. Cassady et al., "Potential Antitumor Agents, Synthesis, Reactivity and Cytotoxicity of α-Methylene Carbonyl Compounds", Journ. Med. Chem., vol. 21, No. 8, pp. 815-819, 1978.
K. H. Lee et al., "Antitumor Agents, 32, Synthesis and Antitumor Activity of Cyclopentenone Derivatives (List continued on next page.)

Primary Examiner—S. J. Friedman
Attorney, Agent, or Firm—Arnold B. Silverman; Jolene W. Appleman

[57] ABSTRACT

Novel 2-(N-substituted-aminoalkyl)-5-(E)-alkylidene cyclopentanones, 2-(N-substituted-aminoalkyl)-5-(E)-arylalkylidene cyclopentanones, and derivatives thereof having the formula

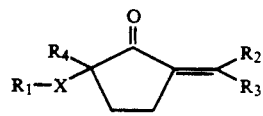

wherein x is methylene or ethylene; $R_1$ is dimethylamino, diethylamino, 1-pyrrolidinyl, 1-piperidinyl, 4-morpholinyl, anilino or substituted anilino; $R_2$ is hydrogen, straight or branched alkyl of 1 to 9 carbon atoms, aryl or arylalkyl; $R_3$ is hydrogen, straight or branched alkyl of 1 to 9 carbon atoms, aryl or arylalkyl; and $R_4$ is hydrogen, methyl, ethyl, allyl, benzyl, substituted benzyl, cyclopentyl, substituted cyclopentyl, cyclopenten-1-yl, or substituted cyclopenten-1-yl; and wherein aryl is phenyl or phenyl substituted with one or more methoxyl, hydroxyl, methylenedioxy, chloro, bromo, fluoro, ethoxycarbonylmethoxy, benzoxy, alkyl group, or their combination, possess anti-inflammatory, analgesic and anticancer properties. The methods of using these compounds to treat inflammation, pain and cancer in mammals and to resist or substantially prevent inflammation and pain in mammals are also disclosed.

6 Claims, No Drawings

OTHER PUBLICATIONS

Related to Helenalin", *Journ. Med. Chem.*, vol. 21, No. 8, pp. 819–822, 1978.

T. G. Waddell et al., "Antitumor Agents: Structure-Activity Relationships in Tenulin Series", *Journ. Pharm. Sci.*, vol. 68, No. 6, pp. 715–718 Jun. 1979.

I. H. Hall et al., "Mode of Action of Sesquiterpene Lactones as Anti-Inflammatory Agents", *Journ. Pharm. Sci.*, vol. 69, No. 5, pp. 537–543, May 1980.

W. Huapu et al., "Anti-Inflammation of MB-2 and its Irritating Effects on Gastrointestinal Tract":, *Bengbu Medical College Journal*, pp. 234–237, Oct. 15, 1991.

Chen et al., Chemical Abstracts, vol. 115 (1991) 1140920.

Zhou et al., Chemical Abstracts, vol. 115 (1990) 114040.

METHOD OF TREATING INFLAMMATION AND PAIN WITH 2-(N-SUBSTITUTED-AMINOALKYL)-5-(E)-ALKYLIDENE CYCLOPENTANONES, 2-(N-SUBSTITUTED-AMINOALKYL)-5-(E)-ARYLALKYLIDENE CYCLOPENTANONES, AND DERIVATIVES THEREOF

This is a division of application Ser. No. 07/847,910, filed Apr. 3, 1992, U.S. Pat. No. 5,250,735.

BACKGROUND OF THE INVENTION

1. Field of the Invention

The present invention relates to 2-(N-substituted-aminoalkyl)-5-(E)-alkylidene cyclopentanones, 2-(N-substituted-aminoalkyl)-5-(E)-arylalkylidene cyclopentanones, and derivatives thereof and their use as anti-inflammatory, analgesic and anticancer agents.

2. Brief Description of the Prior Art

It is known that sesquiterpene lactones, such as, for example, Helenalin, Tenulin and Aromaticin, possess potent anti-inflammatory (T. G. Waddell et al., *J. Pharm. Sci.*, 1979, 68:715; I. H. Hall et al., *J. Pharm. Sci.*, 1980, 69:537) and anticancer (K. H. Lee et al., *Cancer Res.*, 1971, 31:1649; S. M. Kupchan et al., *J. Med. Chem.*, 1971, 14:1147) activities. S. M. Kupchan et al. demonstrated that the presence of an α-methylene-γ-lactone was essential for significant anticancer activity among the sesquiterpene lactones. It has also been shown (G. A. Howie et al., *J. Med. Chem.*, 1976, 19:309) that substitution of an alkyl group at the α-methylene carbon of α-methylene-γ-lactone results in compounds of lower toxicity and higher selectivity. Furthermore, it was shown by I. H. Hall et al. that the α-methylene-γ-lactone moiety within the structure of sesquiterpene lactones, specifically pseudoguaianolide and germacranolide derivatives, was required for activity against carrageenin induced edema inflammation.

While these natural products have potent activities, and a great deal of non-sesquiterpene lactones containing an α-methylene-γ-lactone moiety have been identified and found active, they are unlikely to be of therapeutic value due to their low natural abundance and difficult chemical synthesis. Several attempts (J. M. Cassady et al., *J. Med. Chem.*, 1978, 21:815; K. H. Lee et al., *J. Med. Chem.*, 1978, 21:819) were made to simplify these structures for anticancer activity, but no successful results were obtained.

The prior art discloses several alkylidene and/or alkylamino substituted cyclopentanones and cyclopentenones.

U.S. Pat. No. 3,269,942 (Wilkes) discloses a method for the protection of aqueous media against slime-producing microorganisms which comprises adding to the aqueous media a selected 2,5-bis(N,N-dialkylaminomethyl)cyclopentanone compound. Unlike the present invention, Wilkes discloses no 5-(E)-alkylidene substituted cyclopentanones. Furthermore, Wilkes does not teach a pharmaceutical use for its compounds, but instead employs them for toxicity to slime-producing microorganisms.

U.S. Pat. No. 3,852,296 (Viterbo et al.) discloses selected 2,3-disubstituted Mannich bases of cyclopentanones and cyclopent-2-enones. The compounds are taught as having cholerectic, diuretic, anti-inflammatory and analgesic properties. Unlike the present invention, the compounds of Viterbo et al. have no 5-(E)-alkylidene group and have a substituent at position 3 of the ring.

U.S. Pat. No. 4,766,147 (Noyori et al.) discloses compounds modeled after prostoglandin A and prostoglandin E as pharmaceuticals for the treatment of tumors. The compounds include 5-alkylidene-4-substituted-2-cyclopentenones, 5-(1-hydroxy-aliphatic hydrocarbon)-4-substituted-2-cyclopentenones and 5-alkylidene-3-hydroxy-4-substituted cyclopentanones. Unlike the present invention, the compounds of Noyori et al. do not possess a Mannich base group.

U.S. Pat. No. 4,904,640 (Markert et al.) discloses 2-alkylidene-3,3,5 and 3,5,5-trimethylcyclopentanones as perfumes. Unlike the present invention, the compounds of Markert et al. do not possess a Mannich base group and are substituted at the 3-position of the ring. Furthermore, no pharmacological activity is taught for these compounds.

In spite of these prior disclosures, there remains a very real and substantial need for structurally simple synthetic compounds which maintain the potent anti-inflammatory and anticancer activity exhibited by the sesquiterpene lactones.

SUMMARY OF THE INVENTION

The present invention meets the above-described needs. The present invention provides 5-alkylidene or 5-arylalkylidene cyclopentanones which are substituted at the 2-carbon with N-substituted-aminoalkyl and derivative groups. The compounds of the present invention maintain the potent anti-inflammatory and anticancer activity exhibited by the sesquiterpene lactones and also exhibit analgesic activity. It will be appreciated that the present invention encompasses pharmaceutically acceptable salts of the compounds disclosed herein.

The present invention provides method of treating inflammation, pain and cancer in mammals which comprise administering at least one therapeutically effective dose of a compound of the present invention.

The present invention also provides methods of resisting or substantially preventing inflammation and pain in mammals which comprise administering at least one therapeutically effective dose of a compound of the present invention.

It is an object of the present invention to provide novel 2-(N-substituted-aminoalkyl)-5-(E)-alkylidene cyclopentanones, 2-(N-substituted-aminoalkyl)-5-(E)-arylalkylidene cyclopentanones, and derivatives thereof.

It is an object of the present invention to provide 2-(N-substituted-aminoalkyl)-5-(E)-alkylidene cyclopentanones, 2-(N-substituted-aminoalkyl)-5-(E)-arylalkylidene cyclopentanones, and derivatives thereof which may be administered in one or more therapeutically effective doses to treat, resist or substantially prevent inflammation in mammals.

It is an object of the present invention to provide 2-(N-substituted-aminoalkyl)-5-(E)-alkylidene cyclopentanones, 2-(N-substituted-aminoalkyl)-5-(E)-arylalkylidene cyclopentanones, and derivatives thereof which may be administered in one or more therapeutically effective doses to treat, resist or substantially prevent pain in mammals.

It is an object of the present invention to provide 2-(N-substituted-aminoalkyl)-5-(E)-alkylidene cyclopentanones, 2-(N-substituted-aminoalkyl)-5-(E)-arylalkylidene cyclopentanones, and derivatives thereof which may be administered in one or more therapeutically effective doses to treat cancer in mammals.

It is an object of the present invention to provide a method of treating inflammation in mammals which comprises administering at least one therapeutically effective dose of a selected 2-(N-substituted-aminoalkyl)-5-(E)-alkylidene cyclopentanone, 2-(N-substituted-aminoalkyl)-5-(E)-arylalkylidene cyclopentanone, or derivative thereof.

It is an object of the present invention to provide a method of treating pain in mammals which comprises administering at least one therapeutically effective dose of a selected 2-(N-substituted-aminoalkyl)-5-(E)-alkylidene cyclopentanone, 2-(N-substituted-aminoalkyl)-5-(E)-arylalkylidene cyclopentanone, or derivative thereof.

It is an object of the present invention to provide a method of treating cancer in mammals which comprises administering at least one therapeutically effective dose of a selected 2-(N-substituted-aminoalkyl)-5-(E)-alkylidene cyclopentanone, 2-(N-substituted-aminoalkyl)-5-(E)-arylalkylidene cyclopentanone, or derivative thereof.

It is an object of the present invention to provide a method of resisting or substantially preventing inflammation in mammals which comprises administering at least one therapeutically effective dose of a selected 2-(N-substituted-aminoalkyl)-5-(E)-alkylidene cyclopentanone, 2-(N-substituted-aminoalkyl)-5-(E)-arylalkylidene cyclopentanone, or derivative thereof.

It is an object of the present invention to provide a method of resisting or substantially preventing pain in mammals which comprises administering at least one therapeutically effective dose of a selected 2(N-substituted-aminoalkyl)-5-(E)-alkylidene cyclopentanone, 2-(N-substituted-aminoalkyl)-5-(E)-arylalkylidene cyclopentanone, or derivative thereof.

DESCRIPTION OF THE PREFERRED EMBODIMENTS

"Mammals" as defined herein includes humans.

"Prophylactic use" as defined herein means use to resist or substantially prevent a disease or condition.

The present invention provides 2-(N-substituted-aminoalkyl)-5-(E)-alkylidene cyclopentanones, 2-(N-substituted-aminoalkyl)-5-(E)-arylalkylidene cyclopentanones, and derivatives (A) of the formula

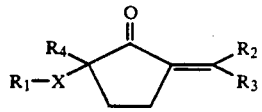

wherein x may be methylene or ethylene, $R_1$ may be dimethylamino, diethylamino, 1-pyrrolidinyl, 1-piperidinyl, 4-morpholinyl, anilino, or substituted anilino, $R_3$ may be hydrogen, straight or branched alkyl of from about 1 to 9 carbon atoms, aryl, or arylalkyl, $R_2$ may be hydrogen, straight or branched alkyl of from about 1 to 9 carbon atoms, aryl, or arylalkyl, and $R_2$ is preferably hydrogen or the same as $R_3$ and if $R_2$ and $R_3$ are ethylene, they may be connected to form a five membered ring, and $R_4$ may be hydrogen, methyl, ethyl, allyl, benzyl, substituted benzyl, cyclopentyl, substituted cyclopentyl, cyclopenten-1-yl, or substituted cyclopenten-1-yl, and wherein aryl is phenyl or phenyl substituted with one or more methoxyl, hydroxyl, methylenedioxy, chloro, bromo, fluoro, ethoxycarbonyl-methoxy, benzoxy, alkyl group, or their combination.

Compounds (A) of the present invention wherein x is methylene may be prepared via an intermediate compound. The intermediate compound may be prepared by reacting an aldehyde or ketone (1) having the formula

wherein $R_3$ may be hydrogen, straight or branched alkyl of from about 1 to 9 carbon atoms, aryl, or arylalkyl, $R_2$ may be hydrogen, straight or branched alkyl of from about 1 to 9 carbon atoms, aryl, or arylalkyl and $R_2$ is preferably hydrogen or the same as $R_3$, and if $R_2$ and $R_3$ are ethylene, they may be connected to form a five membered ring, and wherein aryl is phenyl or phenyl substituted with one or more methoxyl, hydroxyl, methylenedioxy, chloro, bromo, fluoro, ethoxycarbonylmethoxy, benzoxy, alkyl group, or their combination, with cyclopentanone in the presence of alkali at a temperature of from about 20° C. to 70° C. and preferably from about 25° C. to 35° C. to yield an intermediate compound (2) having the formula

wherein $R_2$ and $R_3$ may be as cited above for compound (1).

The intermediate compounds (2) wherein $R_2$ is hydrogen may be prepared alternatively by the Stork enamine reaction of a morpholine enamine of cyclopentanone with an aldehyde. The Stork enamine reaction is well known by those skilled in the art. The reaction may be run for about 4 to 45 hours in refluxing solvent, such as, for example, benzene or toluene. The water generated may be separated by a Dean-Stark trap. The volume of water indicates the extent of the reaction. The Stork enamine reaction is preferable for aldehydes of low reactivity, such as, for example, 2-phenylpropyl aldehyde and 2-formylphenoxyacetic acid ethyl ester, which have large steric effects.

The compounds (A) of the present invention wherein x is methylene, $R_1$ is dimethylamino, diethylamino, 1-pyrrolidinyl, 1-piperidinyl, or 4-morpholinyl, and $R_4$ is hydrogen may be prepared by the Mannich reaction of an intermediate compound (2) with paraformaldehyde and an amine (3) having the formula $R_1H$         (3)

wherein $R_1$ may be dimethylamino, diethylamino, 1-pyrrolidinyl, 1-piperidinyl or 4-morpholinyl. The Mannich reaction is well known by those skilled in the art. The reaction may be run in a lower alkanol, such as, for example, ethanol, with several drops of concentrated HCl by refluxing. When intermediate compound (2) is a liquid, the hydrochloride of compound (A) can be obtained directly from the resulting mixture with high purity, and in most cases further purification is unnecessary. When intermediate compound (2) is a solid, the hydrochloride of compound (A) may be prepared by adding ethanolic hydrogen chloride to the ethereal extract of the corresponding free base, and further purification is needed.

Compounds (A) of the present invention wherein x is methylene, $R_1$ is dimethylamino, diethylamino, 1-piperidinyl, 1-pyrrolidinyl, or 4-morpholinyl, and $R_4$ is methyl, ethyl, allyl, benzyl, substituted benzyl, cyclopentyl, substituted cyclopentyl, cyclopenten-1-yl, or substituted cyclopenten-1-yl may be prepared by a Stork enamine reaction between the chloride of the $R_4$ group and a pyrrolidine enamine of cyclopentanone. The reaction yields a 2-$R_4$ substituted cyclopentanone intermediate compound (4) having the formula

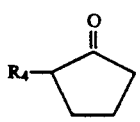

(4)

The intermediate compound (4) may then be reacted with an aldehyde or ketone of formula (1) in a lower alkanol, such as, for example, methanol, in the presence of alkali at about room temperature to yield a 2-$R_4$ substituted-5-(E)-alkylidene or arylalkylidene substituted cyclopentanone intermediate compound (5) having the formula

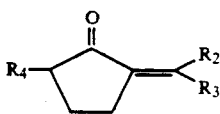

(5)

The intermediate compound (5) may then be reacted with an amine (3) and paraformaldehyde by means of the Mannich reaction to yield a compound (A) wherein x is methylene, $R_1$, is dimethylamino, diethylamino, 1-pyrrolidinyl, 1-piperidinyl, or 4-morpholinyl, $R_2$ and $R_3$ may be as cited above and $R_4$ may be methyl, ethyl, allyl, benzyl, substituted benzyl, cyclopentyl, substituted cyclopentyl, cyclopenten-1-yl, or substituted cyclopenten-1-yl. The reaction may be run in a lower alkanol, such as, for example, ethanol, with several drops of concentrated HCl by refluxing.

When intermediate compound (5) is a liquid, the hydrochloride of compound (A) can be obtained directly from the resulting mixture with high purity, and in most cases further purification is unnecessary. When intermediate compound (5) is a solid, the hydrochloride of compound (A) may be prepared by adding ethanolic hydrogen chloride to the ethereal extract of the corresponding free base, and further purification is needed.

Compounds (A) of the present invention, wherein $R_1$ is anilino or substituted anilino, x is methylene, $R_4$ is substituted or unsubstituted, and $R_2$ and $R_3$ may be as cited above, may be prepared by mixing a compound (A) wherein $R_1$ may be dimethylamino or 4-morpholinyl, x is methylene, $R_4$ is substituted or unsubstituted, and $R_2$ and $R_3$ may be as cited above, with aniline or substituted aniline in 50% ethanol at room temperature for 2 hours. The aniline or substituted aniline exchanges with the dimethylamino or 4-morpholinyl group in the reactant compound (A). The product is a precipitate which can be purified by recrystallization.

The compounds (A) of the present invention wherein x is ethylene and $R_4$ may be hydrogen, allyl, cyclopenten-1-yl or substituted cyclopenten-1-yl may be prepared by adding a compound (6) of the formula

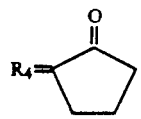

(6)

wherein $R_4$ may be hydrogen, ethylidene, cyclopentylidene, or substituted cyclopentylidene, to a suspension of $NaNH_2$ in an organic solvent, such as, for example, dry toluene, at a temperature below about 30° C. under stirring until no $NH_3$ is evolved and then adding a compound (7) having the formula $R_1CH_2CH_2Cl$ (7)

wherein $R_1$ may be dimethylamino, diethylamino, 1-pyrrolidinyl, 1-piperidinyl or 4-morpholinyl. The mixture may be heated to about 100° C. for about 2 hours under stirring. The product may be extracted with ether to yield an intermediate compound (8) having the formula

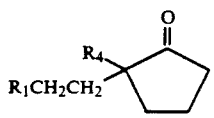

(8)

wherein $R_1$ may be as stated above for compound (7) and $R_4$ may be hydrogen, allyl, cyclopenten-1-yl or substituted cyclopenten-1-yl. Intermediate compound (8) may then be reacted with an aldehyde or ketone of formula (1) in alkali and a lower alkanol, such as, for example, ethanol, at about room temperature under stirring for about 12 hours. The product may be extracted with ether to yield a compound (A) wherein x is ethylene, $R_1$, $R_2$, and $R_3$ may be as cited above, and $R_4$ may be hydrogen, allyl, cyclopenten-1-yl or substituted cyclopenten-1-yl.

The compounds (A) of the present invention are useful as anti-inflammatory, analgesic and anticancer agents in mammals. It is believed that the physiochemical reactions leading to anticancer activity in one group of the compounds (A) has been determined. In the compounds (A) of the present invention wherein x is methylene and $R_4$ is hydrogen, the disubstituted-aminomethyl group can serve as a masked α-methylene group in addition to being able to form pharmaceutically acceptable salts. In this fashion, the disubstituted-aminomethyl group can undergo deamination. The α-methylene cyclopentanone thus formed is capable of undergoing a Michael addition reaction with cellular nucleophiles, such as thiol-containing enzymes, and inhibiting tumor cell growth. Michael addition reactions are well known by those skilled in the art. The 5-(E)-alkylidene or arylalkylidene group potentiates the overall antitumor activity and provides a certain degree of selectivity among normal cells and different tumor cells.

For anti-inflammatory activity of the compounds (A) wherein x is methylene, the formation of an α-methylene cyclopentanone intermediate by deamination is not necessary. Thus the H at R4 can be substituted by alkyl, aryl, or other substituents. In fact, to focus on anti-inflammatory activity, it is desirable to have a substituent at $R_4$ so that the compound is unlikely to deaminate to form an α-methylene group and is therefore unlikely to cause cytotoxic side-effects. Those compounds (A)

wherein x is methylene and $R_4$ is substituted exhibit lower anticancer activity as compared to those compounds (A) wherein x is methylene and $R_4$ is hydrogen. However, the $R_4$-substituted aminomethyl compounds (A) show higher selectivity.

In another embodiment of the present invention, compounds (A) are provided wherein x is ethylene. In most cases, replacing the N-substituted-aminomethyl group with an N-substituted-aminoethyl group reduces cytotoxicity by reducing deamination and formation of an α-methylene group. However, compounds (A) wherein x is ethylene and $R_4$ is cyclopenten-1-yl or substituted cyclopenten-1-yl exhibit significant anticancer activity through a different physiochemical reaction.

The present invention provides methods of treating inflammation, pain and cancer in mammals by administering at least one therapeutically effective dose of a compound (A). The compounds (A) may be administered, for example, orally, intraveneously, rectally, intramuscularly and subcutaneously. A therapeutically effective oral dosage is from about 10 to 300 mg/kg body weight, and a therapeutically effective parenteral dosage is from about 5 to 50 mg/kg body weight. Depending upon the nature of the illness and the condition of the patient, one or more therapeutically effective doses of the compound may be administered at prescribed dosages and frequencies which may be readily determined by those skilled in the art. Acute toxicity of the compounds is low.

The preparations of the compounds (A) for administration may take the dosage form of, for example, pills, tablets, powders or granules. Compatible pharmaceutical additives such as, for example, sugars, starches, cellulose, lubricants, sweeteners, coloring agents and stabilizers may be added. Preparations of the compounds (A) for injection may take the form of, for example, aqueous solutions, suspensions or emulsions. Due to the compounds' limited stability in water, preparations for injection should be used soon after preparation.

It will be appreciated that compounds (A) of the present invention may be used prophylactically. The present invention provides methods of resisting or substantially preventing inflammation and pain in mammals by administering at least one therapeutically effective dose of a compound (A).

The following examples are given for the purpose of illustrating this invention and are not intended as limitations thereof.

EXAMPLE 1

The following is an example of a method of preparing 2-Dimethylaminomethyl-5-(E)-pentylidene cyclopentanone hydrochloride:

A stirred solution of 42.0 grams (g) (0.5 mole) of cyclopentanone in 80 milliliters (ml) of 1 percent (%) NaOH was treated with 21.5 g (0.25 mole) of n-pentanal at about 30 degrees Celsius (°C.). After stirring for about 2 hours, the solution was neutralized with 36% acetic acid, then extracted with three 30 ml portions of benzene. Then 1.0 ml of phosphoric acid was added to the combined extracts. After the resulting mixture was refluxed through a condenser equipped with a Dean-Stark trap for about 2 hours, the solvent was removed on a rotary evaporator to give an oil residue, which was subjected to distillation to give 28.5 g of 2-(E)-pentylidene cyclopentanone as a yellowish liquid. The boiling point of this intermediate compound was determined to be 98°–102° C. at a pressure of 6 millimeters (mm) mercury (Hg).

4.1 g of dimethylamine hydrochloride, 3.7 g of paraformaldehyde and 20 ml of ethanol were added with 5 drops of concentrated hydrochloric acid to 7.6 g of 2-(E)-pentylidene cyclopentanone. After refluxing for about 2 hours, the resulting solution was mixed with 2.2 g of paraformaldehyde and then refluxed for about 2 additional hours. The solution was treated with activated charcoal and filtered. The filtrate was allowed to stand overnight, filtered and washed with cold ether containing a small amount of absolute ethanol to give 7.7 g of 2-Dimethylaminomethyl-5-(E)-pentylidene cyclopentanone hydrochloride as colorless leaflets. The melting point of the product was determined to be 156°–157° C.

EXAMPLE 2

The following is an example of a method of preparing 2-Dimethylaminomethyl-5-(E)-octylidene cyclopentanone hydrochloride:

The procedure was similar to that in Example 1 by reacting n-octanal with cyclopentanone in the presence of 1% NaOH to give 2-(E)-octylidene cyclopentanone. The boiling point of this intermediate compound was determined to be 120°–125° C. at a pressure of 4 mm Hg. A subsequent Mannich reaction yielded the 2-Dimethylaminomethyl-5-(E)-octylidene cyclopentanone hydrochloride. The melting point of the product was determined to be 138°–140° C.

EXAMPLE 3

The following is an example of a method of preparing 2-Dimethylaminomethyl-5-(1-methylethylidene) cyclopentanone hydrochloride:

A mixture of 190 ml of acetone and 36.0 g of sodium hydroxide in 600 ml of water was treated with 60.0 g of cyclopentanone under stirring. After stirring for about 12 hours at about room temperature, the mixture was neutralized with 36% acetic acid and extracted with three 60 ml portions of ether. The combined extracts were dried over anhydrous magnesium sulfate and evaporated to give a residue. The residue was distilled to obtain 62.6 g of 2-(1-methylethylidene) cyclopentanone as a colorless liquid. The boiling point of this intermediate compound was determined to be 85°–88° C. at a pressure of 10 mm Hg. A subsequent Mannich reaction yielded the 2-Dimethylaminomethyl-5-(1-methylethylidene) cyclopentanone hydrochloride. The melting point of the product was determined to be 173°–175° C.

EXAMPLE 4

The following is an example of a method of preparing 2-Dimethylaminomethyl-5-(E)-(2-ethoxycarbonylmethoxyl-benzylidene) cyclopentanone hydrochloride:

A solution of 21.2 g of morpholine enamine of cyclopentanone, 24.0 g of 2-formylphenoxyacetic acid ethyl ester, and 200 ml of benzene was refluxed through a condenser equipped with a Dean-Stark trap for about 4.5 hours. The resulting solution was cooled to about room temperature, and treated with 35 ml of 6 normal (N) hydrochloric acid. After stirring for about 2 hours at about room temperature, the benzene layer was separated and the aqueous layer was extracted with two 15 ml portions of benzene. The combined benzene layer and extracts were washed with 5% sodium bicarbonate and saturated sodium chloride solution and dried over anhydrous magnesium sulfate. After removal of the solvent in vacuo, 27.6 g of nearly pure product was obtained. The product was crystallized in 50% ethanol to give 26.0 g of 2-(E)-2-ethoxycarbonylmethoxyl-benzylidene) cyclopentanone as colorless crystals. The melting point of this intermediate compound was determined to be 77°-79° C.

2.0 g of dimethylamine hydrochloride, 1.8 g of paraformaldehyde and 30 ml of ethanol were added with 3 drops of concentrated hydrochloric acid to 6.5 g of 2-(E)-(2-ethoxycarbonylmethoxylbenzylidene) cyclopentanone. After refluxing for about 2 hours, the resulting solution was treated with 0.7 g of paraformaldehyde and then refluxed for about 2 additional hours. After the solvent was removed in vacuo, a syrupy residue was obtained. Then 100 ml of water was added to the residue, stirred for about 10 minutes, and filtered. The filtrate was adjusted to about pH 9 by the addition of 10% sodium carbonate solution and extracted with three 20 ml portions of ether. The aqueous layer was again treated with 10% sodium carbonate solution to about pH 11 and extracted with two additional 20 ml portions of ether. The combined ether was dried over anhydrous magnesium sulfate and treated with ethanolic hydrogen chloride. It was filtered to give 4.7 g of product. Recrystallization from absolute ethanol-acetone gave 4.2 g of 2-Dimethylaminomethyl-5-(E)-(2-ethoxycarbonylmethoxyl-benzylidene) cyclopentanone hydrochloride as a white powder product. The melting point of the product was determined to be 124°-126° C.

EXAMPLE 5

The following is an example of a method of preparing 2-Dimethylaminomethyl-5-(E)-[2-(3-bromophenyl) propylidene] cyclopentanone hydrochloride:

The procedure was similar to that in Example 4 by reacting 2-(3-bromophenyl) propyl aldehyde with the morpholine enamine of cyclopentanone to give 2-(E)-[2-(3-bromophenyl) propylidene] cyclopentanone as a yellowish liquid. The boiling point of this intermediate compound was determined to be 165°-170° C. at a pressure of 1 mm Hg. A subsequent Mannich reaction yielded the 2-Dimethylaminomethyl-5-(E)-[2-(3-bromophenyl) propylidene] cyclopentanone hydrochloride. The melting point of the product was determined to be 135°-137° C.

EXAMPLE 6

The following is an example of a method of preparing 2-Dimethylaminomethyl-5-(E)-benzylidene cyclopentanone hydrochloride:

The procedure was similar to that in Example 4 by reacting benzaldehyde with the morpholine enamine of cyclopentanone to give 2-(E)-benzylidene cyclopentanone. The melting point of this intermediate compound was determined to be 67°-69° C. A subsequent Mannich reaction yielded the 2-Dimethylaminomethyl-5-(E)-benzylidene cyclopentanone hydrochloride. The melting point of the product was determined to be 153°-155° C.

EXAMPLE 7

The following is an example of a method of preparing 2-Dimethylaminomethyl-5-(E)-[(2-methoxy) benzylidene] cyclopentanone hydrochloride:

The procedure was similar to that in Example 4 by reacting 2-methoxybenzaldehyde with the morpholine enamine of cyclopentanone to give 2-(E)-[(2-methoxy) benzylidene] cyclopentanone. The melting popint of this intermediate compound was determined to be 80°-82° C. A subsequent Mannich reaction yielded the 2-Dimethylaminomethyl-5-(E)-[(2-methoxy) benzylidene] cyclopentanone hydrochloride. The melting point of the product was determined to be 167°-169° C.

EXAMPLE 8

The following is an example of a method of preparing 2-Dimethylaminomethyl-5-(E)-[(4-hydroxy) benzylidene] cyclopentanone hydrochloride:

The procedure was similar to that in Example 4 by reacting 4-hydroxybenzaldehyde with the morpholine enamine of cyclopentanone to give 2-(E)-[(4-hydroxy) benzylidene] cyclopentanone. The melting point of this intermediate compound was determined to be 188°-190° C. A subsequent Mannich reaction yielded the 2-Dimethylaminomethyl-5-(E)-[(4-hydroxy) benzylidene] cyclopentanone hydrochloride. The melting point of the product was determined to be 174°-175° C.

EXAMPLE 9

The following is an example of a method of preparing 2-[(4-Chlorophenyl) aminomethyl]-5-(E)-[(4-hydroxy) benzylidene] cyclopentanone:

A solution of 1.0 millimoles (mmole) of the final product in Example 8 was made in 12 ml of 50% ethanol and mixed with a 12 ml 50% ethanolic solution of 1.0 mmole of 4-chloro-aniline. The resulting solution was left to stand for about 2 hours at room temperature. The precipitate was collected by filtration, washed with water and recrystallized from ethyl acetate to give the 2-[(4-Chlorophenyl) aminomethyl]-5-(E)-[(4-hydroxy) benzylidene] cyclopentanone.

EXAMPLE 10

The following is an example of a method of preparing 2-Morpholinomethyl-5-(E)-[(2-methoxy) benzylidene] cyclopentanone hydrochloride:

A solution of 5 mmole of the final product in Example 7 was made in 25 ml of 50% ethanol and mixed with a 25 ml 50% ethanolic solution of 5 mmole of morpholine. The mixture was stirred at about room temperature for about 2 hours. The resulting precipitate was collected by filtration and recrystallized in ethanol-HCl to give the 2-Morpholinomethyl-5-(E)-[(2-methoxy) benzylidene] cyclopentanone hydrochloride. The melting point of the product was determined to be 155°-156° C.

EXAMPLE 11

The following is an example of a method of preparing 2-Benzyl-2-dimethylaminomethyl-5-(E)-[(2-methoxy) benzylidene] cyclopentanone hydrochloride:

A Stork reaction between benzyl chloride and the pyrrolidine enamine of cyclopentanone gave 2-benzyl-cyclopentanone. The boiling point of this intermediate compound was determined to be 121°-125° C. at a pressure of 2 mm Hg. To a solution containing 32 mmole of 2-benzylcyclopentanone and 48 mmole of 2-methoxybenzaldehyde in 20 ml of methanol was added 12 ml of 5% NaOH with stirring at about room temperature. After about 2 hours of stirring, the mixture was cooled and the precipitate was collected by filtration and washed with water. The solid was recrystallized in ethanol to give 2-benzyl-5-(E)-[(2-methoxy) benzylidene] cyclopentanone. The melting point of this intermediate product was determined to be 65°-67° C. A mixture containing 20 mmole of this intermediate, 38 mmole of dimethylamine hydrochloride, 2.4 g of paraformaldehyde and 4 drops of concentrated HCl in 50 ml of ethanol was refluxed with stirring. After about 12 hours, 1.8 g of paraformaldehyde was added and refluxing was continued for about 12 additional hours. The resulting solution was concentrated in vacuo to give a residue. Then 100 ml of water was added to the residue and stirred for about 15 minutes at about room temperature. The precipitate was removed by filtration. The resulting filtrate was treated with 10% NaOH to about pH 10 and extracted with ether. The extract was dried over anhydrous MgSO4 and acidified with ethanolic HCl to give a precipitate. The precipitate was recrystallized in a mixture of methanol and acetone to yield the 2-Benzyl-2-dimethylaminomethyl-5-(E)-[(2-methoxy) benzylidene] cyclopentanone hydrochloride. The melting point of the product was determined to be 175°–177° C.

EXAMPLE 12

The following is an example of a method of preparing 2-Benzyl-2-dimethylaminomethyl-5-(E)-[(4-methoxy) benzylidene] cyclopentanone hydrochloride:

The procedure was similar to that in Example 11 except that 4-methoxybenzaldehyde was used in the place of 2-methoxybenzaldehyde. The 2-Benzyl-2-dimethylaminomethyl-5-(E)-[(4-methoxy) benzylidene] cyclopentanone hydrochloride had a melting point of 164°–166° C.

EXAMPLE 13

The following is an example of a method of preparing 2-(1-Cyclopenten-1-yl)-2-dimethylaminoethyl-5-(E)-[(4-chloro) benzylidene] cyclopentanone hydrochloride:

To a suspension of 1.90 g (41 mmole) of NaNH2 in 60 ml of dry toluene, 5.50 g (35 mmole) of 2-cyclopentylidene cyclopentanone was added dropwise below about 30° C. under stirring. The resulting mixture was stirred at about room temperature until no NH3 was evolved and then 3.8 g (32 mmole) of 2-dimethylaminoethyl chloride was added dropwise. The mixture was heated for about 2 hours at about 100° C. under stirring. On cooling, the mixture was acidified with 2N HCl. The aqueous layer was separated and the organic layer was extracted with 2N HCl. The combined aqueous layer was basified with 10% NaOH and extracted with ether. The ether extracts were dried over anhydrous MgSO4. The ether solution was treated with ethanolic hydrogen chloride to give 2-(1-cyclopenten-1-yl)-2-dimethylamino-ethyl cyclopentanone hydrochloride.

To a solution of 1.0 g (3.9 mmole) of 2-(1-cyclopenten-1-yl)-2-dimethylaminoethyl cyclopentanone hydrochloride and 8.1 mmole of 4-chloro-benzaldehyde in 40 ml of ethanol, 3.2 ml of 5N NaOH was added dropwise. The resulting mixture was stirred at about room temperature for about 12 hours and then mixed with 60 ml of water and extracted with ether. The ether extract was extracted with 6N HCl. The HCl extract was basified and extracted with ether, and then dried over anhydrous MgSO4. The ether solution was treated with ethanolic hydrogen chloride to give a precipitate, which was recrystallized from ethanol to give the 2-(1-Cyclopenten-1-yl)-2-dimethylaminoethyl-5-(E)-[(4-chloro) benzylidene] cyclopentanone hydrochloride. The melting point of the product was determined to be 234°–236° C.

The compounds of Examples 1–13 may be provided in whatever dosage form is desired by means known to those skilled in the art.

EXAMPLE 14

Anti-inflammatory activity was evaluated by examining the inhibitory activity of candidate compounds on carrageenin-induced rat paw edema according to a literature procedure [C. A. Winter, et al., Proc. Soc. Exp. Biol. Med. 111, 544 (1962)]. Test compounds were orally administered about 1 hour or subcutaneously injected about 0.5 hours before the injection of 100 microliters of a 1% suspension of carrageenin in saline into the subcutaneous tissues of the right hind paw of Wistar rats. The paw volumes were measured about 3 hours after carrageenin injection. The paw volumes were compared with that of a control group to give the percentage of inflammation inhibition. The results of these tests are shown in Table I. "Compound numbers" refer to compounds whose synthesis is illustrated in the corresponding Example number. The P values are the results of T-tests, which are well known to those skilled in the art.

TABLE I

Anti-inflammatory Activity on Carrageenin Induced Rat Paw Edema

| Compound Number | Dose mg/kg | Number of Rats | Inhibition % | P< |
|---|---|---|---|---|
| 6 | 50.0 (sc) | 4 | 77.4 | 0.01 |
| 7 | 50.0 (sc) | 4 | 95.8 | 0.001 |
|   | 25.0 (sc) | 6 | 70.3 | 0.001 |
|   | 12.5 (sc) | 6 | 44.2 | 0.01 |
| 8 | 50.0 (sc) | 4 | 95.9 | 0.001 |
| 11 | 96.0 (po) | 5 | 52.2 | 0.01 |
| 12 | 96.0 (po) | 5 | 57.3 | 0.01 |
| Ibuprofen | 25.0 (sc) | 6 | 72.9 | 0.001 |
|   | 52.0 (po) | 6 | 54.9 | 0.01 | sc - subcutaneous
po - oral

Table I demonstrates that compounds of the present invention produced significant inhibition of carrageenin induced rat paw edema as compared to a control group. The inhibition produced by the compounds of the present invention compared favorably with, and in some instances superior to, ibuprofen.

EXAMPLE 15

Analgesic activity was evaluated by a procedure similar to that described by Koster et al. [R. Koster, et al., Fed. Proc., 18, 412 (1959)]. About one hour after oral administration of test compounds to mice, 0.1 ml/10 g body weight of acetic acid was intraperitoneally injected. About five minutes later, the number of writhes of each mouse was counted for a period of about 20 minutes. The analgesic effect was manifested as a reduction in the number of writhes. The results of these tests are shown in Table II. "Compound numbers" refer to compounds whose synthesis is illustrated in the corresponding Example number. The P values are the results of T-tests, which are well known to those skilled in the art.

TABLE II

| Analgesic Activity on Acetic Acid Induced Mouse Writhes | | | |
|---|---|---|---|
| Compound Number | Dose mg/kg | Number of Mice | Inhibition % | P |
| 11 | 96 | 8 | 41.7 | 0.05 |
| 12 | 96 | 8 | 86.6 | 0.01 |
|    | 48 | 8 | 45.6 | 0.05 |
| Aspirin | 100 | 8 | 46.7 | 0.05 |
|    | 200 | 8 | 64.0 | 0.01 | cellular sensitivity index was calculated by taking the difference between the logarithm of $GI_{50}$ (or TGI, $LC_{50}$) value for a cell line versus the arithmetic mean of the logarithm of $GI_{50}$ (or TGI, $LC_{50}$) value for all cell line responses measured for a given compound. A differential cellular sensitivity index of greater than 3 means that a compound is highly selective towards the tumor cell line of certain cancer types, while the value of less than 1 means low selectivity. The results of these tests are shown in Table III. "Compound numbers" refer to compounds whose synthesis is illustrated in the corresponding Example number.

TABLE III

| | Tumor Cell Screening Data | | | | | |
|---|---|---|---|---|---|---|
| Compound Number | Mean Response Of All Cell Lines (Log) | | | Differential Cellular Sensitivity* | | |
| | $GI_{50}$ | TGI | $LC_{50}$ | $GI_{50}$ | TGI | $LC_{50}$ |
| 1 | −5.80 | −5.42 | −4.96 | 1.05 | 1.13 | 1.29 |
| | | | | LEU;COL | COL;REN | COL;LNS;REN |
| 2 | −5.29 | −4.91 | −4.48 | 0.80 | 0.61 | 0.77 |
| | | | | LEU;COL | COL;REN | COL;LNS;REN |
| 3 | −4.72 | −4.39 | −4.17 | 1.99 | 2.01 | 1.92 |
| | | | | LEU | COL;LEU | SCL |
| 4 | −5.20 | −4.80 | −4.40 | 1.00 | 0.70 | 0.90 |
| | | | | LEU | LEU | CNS;LNS;MEL |
| 5 | −4.90 | −4.56 | −4.20 | 0.86 | 0.72 | 0.25 |
| | | | | LEU | LEU | CNS;OVA |
| 7 | −5.20 | −4.80 | −4.40 | 0.70 | 0.60 | 0.80 |
| | | | | LEU | COL | COL |
| 8 | −5.37 | −4.97 | −4.44 | 0.94 | 0.69 | 0.81 |
| | | | | COL;LEU | LEU | CNS;REN;SCL |
| 9 | −5.50 | −5.00 | −4.51 | 1.35 | 0.87 | 0.89 |
| | | | | COL;LEU;SCL | LEU;SCL | COL |
| 10 | −5.10 | −4.71 | −4.28 | 1.11 | 0.86 | 1.01 |
| | | | | LEU;COL | LEU | MEL;REN;OVA |
| 11 | −5.66 | −4.60 | −4.08 | 1.30 | 1.52 | 1.26 |
| | | | | LEU;COL | LEU | COL |
| 12 | −4.45 | −4.11 | −4.01 | 0.36 | 0.37 | 0.15 |
| | | | | COL;MEL | LEU;SCL | SCL |
| 13 | −5.15 | −4.72 | −4.35 | 0.60 | 0.74 | 0.82 |
| | | | | MEL | MEL | MEL |

*Tumor cell line subpanels are identified as follows:
LEU = Leukemia/lymphoma
LNS = Non-small cell lung
COL = Colon
MEL = Melanoma
OVA = Ovary
REN = Kidney
SCL = Small cell lung Table II demonstrates that compounds of the present invention produced a significant reduction in acetic acid induced mouse writhes. The inhibition produced by the compounds of the present invention compared favorably with, and in some instances superior to, aspirin.

EXAMPLE 16

Samples were submitted to the National Cancer Institute and tested against 60 human tumor cell lines derived from several cancer types (leukemia, lung, colon, melanoma, renal, ovarian, brain) using in vitro screen assays described by Boyd, M. R. (*Proc. Am. Assoc. Cancer Res.*, 30: 652, 1989). In the assay, a candidate compound was tested for its ability to inhibit tumor cell growth. A dose response curve of percent cell growth versus compound concentration over a concentration range of $10^{-9}$ to $10^{-4}$ molar of each test compound was established to determine $GI_{50}$, TGI and $LC_{50}$. $GI_{50}$ and TGI denote that cell proliferation was inhibited by 50% and 100% respectively. $LC_{50}$ denotes that 50% of cell population was killed. The selectivity of a compound towards a certain type of tumor cell line was evaluated from mean graphs which compared the relative drug concentrations required to produce the same level of response (e.g. $GI_{50}$) in each cell line. A differential Table III demonstrates that compounds of the present invention produced a significant growth inhibition and killing of tumor cells at concentration levels of below $10^{-4}M$ (i.e., mean log values of $GI_{50}$, TGI and $LC_{50}$ less than −4). The response produced by the compounds of the present invention compared favorably with, and in most instances superior to, 5-fluorouracil which is a well known anticancer agent having mean log $LC_{50}$ of −3.5. As evidenced in Table III, the compounds of the present invention exhibited varying degrees of differential cellular sensitivity towards different cell line subpanels, thus demonstrating their selectivity in inhibiting different tumor cells.

EXAMPLE 17

Antitumor effect was measured on Ehrlich ascites carcinoma. Ehrlich ascites carcinoma cells were intraperitoneally administered to ICR mice. After 24 hours, 20 mg/kg/day of the compound whose synthesis is illustrated in Example 1 and Example 2 were each administered to the mice by intraperitoneal route for 9 days. The periods of survival of these animals were examined.

When the compound of Example 1 was administered, the average number of days of survival was 41±5.4 days. The increase of life span (ILS %) was 173.8% over the control, and the ratio of survival for more than 40 days was 9/11.

When the compound of Example 2 was administered, the average number of days of survival was 33±8.2 days. The increase of life span (ILS %) was 112.0% over the control, and the ratio of survival for more than 40 days was 3/9.

EXAMPLE 18

The acute toxicity of one typical compound of this invention was measured by administering the compound to a group of 4 week old male mice. The compound whose synthesis is illustrated in Example 1 showed an $LD_{50}$ of 486 mg/kg body weight by the oral route of administration, an $LD_{50}$ of 107 mg/kg body weight by the intraperitoneal route of administration, and an $LD_{50}$ of 52 mg/kg body weight by the intravenous route of administration. These results show that the compound of this invention has low acute toxicity.

It will be appreciated that the present invention provides novel 2-(N-substituted-aminoalkyl)-5-(E)-alkylidene cyclopentanones, 2-(N-substituted-aminoalkyl)-5-(E)-arylalkylidene cyclopentanones, and derivatives thereof.

It will be appreciated that compounds of the present invention are readily adaptable to use as pharmaceuticals for the treatment of inflammation, pain and cancer in mammals, including humans.

It will be further appreciated that compounds of the present invention are readily adaptable to use as pharmaceuticals for resisting or substantially preventing inflammation and pain in mammals, including humans.

It will be appreciated that the present invention provides methods of treating inflammation, pain and cancer in mammals which comprise administering at least one therapeutically effective dose of a compound of the present invention.

It will be further appreciated that the present invention provides methods of resisting or substantially preventing inflammation and pain in mammals which comprise administering at least one therapeutically effective dose of a compound of the present invention.

Whereas particular embodiments of the present invention have been described above, for purposes of illustration, it will be evident to those skilled in the art that numerous variations of the details may be made without departing from the invention as defined in the appended claims.

What is claimed is:

1. A method of treating inflammation in a mammal comprising:
   administering to said mammal at least one therapeutically effective dose of a compound of the formula

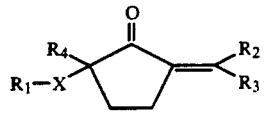

and pharmaceutically acceptable salts thereof, wherein x is methylene; $R_1$ is dimethylamino; $R_2$ is hydrogen; $R_3$ is straight or branched alkyl of 1 to 9 carbon atoms; and $R_4$ is hydrogen.

2. The method of claim 1, including administering at least one therapeutically effective dose of said compound to a human.

3. A method of resisting inflammation in a mammal comprising:
   administering to said mammal at least one therapeutically effective dose of a compound of the formula

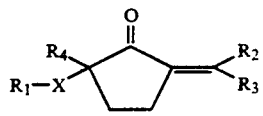

and pharmaceutically acceptable salts thereof, wherein x is methylene; $R_1$ is dimethylamino; $R_2$ is hydrogen; $R_3$ is straight or branched alkyl of 1 to 9 carbon atoms; and $R_4$ is hydrogen.

4. A method of treating pain in a mammal comprising:
   administering to said mammal at least one therapeutically effective dose of a compound of the formula

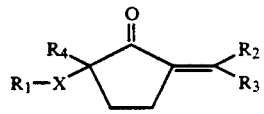

and pharmaceutically acceptable salts thereof, wherein x is methylene; $R_1$ is dimethylamino; $R_2$ is hydrogen; $R_3$ is straight or branched alkyl of 1 to 9 carbon atoms; and $R_4$ is hydrogen.

5. The method of claim 4, including administering at least one therapeutically effective dose of said compound to a human.

6. A method of resisting pain in a mammal comprising:
   administering at least one therapeutically effective dose of a compound of the formula

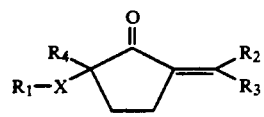

and pharmaceutically acceptable salts thereof, wherein x is methylene; $R_1$ is dimethylamino; $R_2$ is hydrogen; $R_3$ is straight or branched alkyl of 1 to 9 carbon atoms; and $R_4$ is hydrogen.

* * * * *